United States Patent
Rivard et al.

(12) 
(10) Patent No.: US 6,638,060 B1
(45) Date of Patent: Oct. 28, 2003

(54) EVERLASTING CANDLE

(75) Inventors: David Rivard, Richmond (CA); Ojong Setiawan, Richmond (CA)

(73) Assignee: Enchanted Meadow Products Inc., Richmond (CA)

( * ) Notice: Subject to any disclaimer, the term of this patent is extended or adjusted under 35 U.S.C. 154(b) by 0 days.

(21) Appl. No.: 10/268,779

(22) Filed: Oct. 11, 2002

Related U.S. Application Data
(60) Provisional application No. 60/392,265, filed on Jul. 1, 2002.

(51) Int. Cl.[7] .................................................. F23D 3/16
(52) U.S. Cl. ....................... 431/289; 431/291; 431/126; 362/161
(58) Field of Search ................................ 431/288–295, 431/126; 362/161, 182, 173; D26/9.11

(56) References Cited

U.S. PATENT DOCUMENTS

| | | | | |
|---|---|---|---|---|
| 6,036,477 A | * | 3/2000 | Frandsen | 431/289 |
| 6,059,564 A | * | 5/2000 | Morris | 431/291 |
| 6,375,455 B2 | * | 4/2002 | Frandsen | 431/289 |
| 6,435,694 B1 | * | 8/2002 | Bell et al. | 431/291 |
| 6,474,980 B2 | * | 11/2002 | LaVanier | 431/126 |

FOREIGN PATENT DOCUMENTS

| | | |
|---|---|---|
| CA | 2125118 | 3/2002 |

\* cited by examiner

*Primary Examiner*—James C. Yeung
(74) *Attorney, Agent, or Firm*—Robert H. Barrigar

(57) ABSTRACT

An everlasting candle comprising a wax body with a recessed hollow in its top for receiving an insulating container, and a smaller holding container with an annular rim set within the insulating container and communicating with the insulating container only by the rim (thereby to provide an insulative airspace between the two containers), the holding container being suitably dimensioned to replaceably receive a tea light votive candle. In use, the replaceable tea light votive candle within the everlasting candle burns with the same flame as a conventional paraffin candle, and will be liquefied and consumed during use. However, since the main wax body of the everlasting candle is separate and insulated from the replaceable tea light votive candle, the wax body of the everlasting candle will not be liquefied or consumed. Preferably, the holding container is constructed of metal, and the rim of the holding container includes a groove into which scented aromatherapy oils or the like may be placed so as to diffuse into the air. The heat of the burning tea light votive candle warms the metal holding container, thereby accelerating the evaporation of the scented oil.

2 Claims, 2 Drawing Sheets

EVERLASTING CANDLE

RELATED APPLICATION

This application is the successor to provisional U.S. patent application Ser. No. 60/392,265 filed Jul. 1, 2002, and applicant claims domestic priority under 35 USC §119(e) based upon such provisional application.

FIELD OF THE INVENTION

The present invention relates to candles, and in particular to a reusable candle, the wax body of which is not consumed during use.

BACKGROUND OF THE INVENTION

It is well known that the burning of conventional paraffin or other wax candles involves the liquefaction, deformation and consumption of the candle itself. The expectation of such deformation and consumption may make the decision of whether or not to light a conventional candle a difficult one to make, particularly in the case of expensive ornamental candles. Liquified wax also frequently runs down the sides of a conventional candle, thereby creating a mess, damaging furniture, and potentially constituting a fire hazard.

Liquid fuel lamps that are made to appear like candles are also known in the prior art, but their use entails other disadvantages that are discussed below. By way of example, Canadian Patent No. 2,125,118 entitled Reusable Candle discloses a lamp of the sort having an internal reservoir structure that is refillable with a liquid fuel. The body of the lamp (that surrounds the internal reservoir) is made of wax so that the lamp may resemble a conventional candle.

It will be appreciated that the filling of liquid fuel candle lamps entails some hazard to the user because the liquid fuel is combustible and poisonous, and may be spilled and unintentionally set ablaze, or may present a poison hazard if ingested. Filling the reservoir of a liquid fuel candle lamp is also messy and prone to spillage, and spilled liquid fuel may ruin the finish of the wax body of the lamp or surrounding articles. It is also noted that the flame that is produced by a liquid fuel lamp is visibly distinguishable from the flame produced by a conventional paraffin candle, partly because the flame is positioned above a protruding glass tube that holds the wick end sufficiently above the wax body to keep the latter from melting.

It is accordingly one object of the present invention to provide an everlasting candle that looks and burns like a conventional candle, but whose body is not liquified or consumed during use.

SUMMARY OF THE INVENTION

In accordance with one aspect of the present invention, there is provided an everlasting candle comprising a wax body with a recessed hollow in its top for receiving an insulating container, and a smaller holding container with an annular rim set within the insulating container and communicating with the insulating container only by the rim (thereby to provide an insulative airspace between the underside and lower side walls of the holding container and the neighbouring inner walls and floor of the insulating container), the holding container being suitably dimensioned to replaceably receive a conventional tea light votive candle and to ensure that any molten wax from the tea light votive candle does not spill into the insulative airspace. The insulating container is preferably constructed of plastic or some other material having a high specific heat capacity to further preclude the transfer of heat through to the wax body. The holding container may be constructed of a similar material, but may also be constructed of metal or other materials without regard to specific heat capacity.

When lit, the replaceable tea light votive candle within the everlasting candle will, of course, burn with the same flame as a conventional paraffin candle, and will be liquefied and consumed during use. However, since the main wax body of the everlasting candle is separate and insulated from the replaceable tea light votive candle, the wax body of the everlasting candle will not be liquefied or consumed. In appearance, the everlasting candle of this invention is distinguishable from a conventional candle (whether lit or not) only by the presence of the rim of the holding container.

In a preferred embodiment, the holding container is constructed of metal, and the rim of the holding container includes a groove into which scented aromatherapy oils or the like may be placed so as to diffuse into the air. In use, the heat of the burning tea light votive candle warms the metal holding container, thereby accelerating the evaporation of the scented oil.

The insulating container may protrude slightly above the top of the wax body (especially if the holding container is made of metal) so as to maintain the holding container sufficiently separate from the wax body as to prevent melting, and the lip of the insulating container and/or the rim of the holding container is, in a preferred embodiment, notched to allow warm air to escape from between the container walls and to draw cooling air in to replace it.

DETAILED DESCRIPTION OF THE PREFERRED EMBODIMENT

Figure 1:
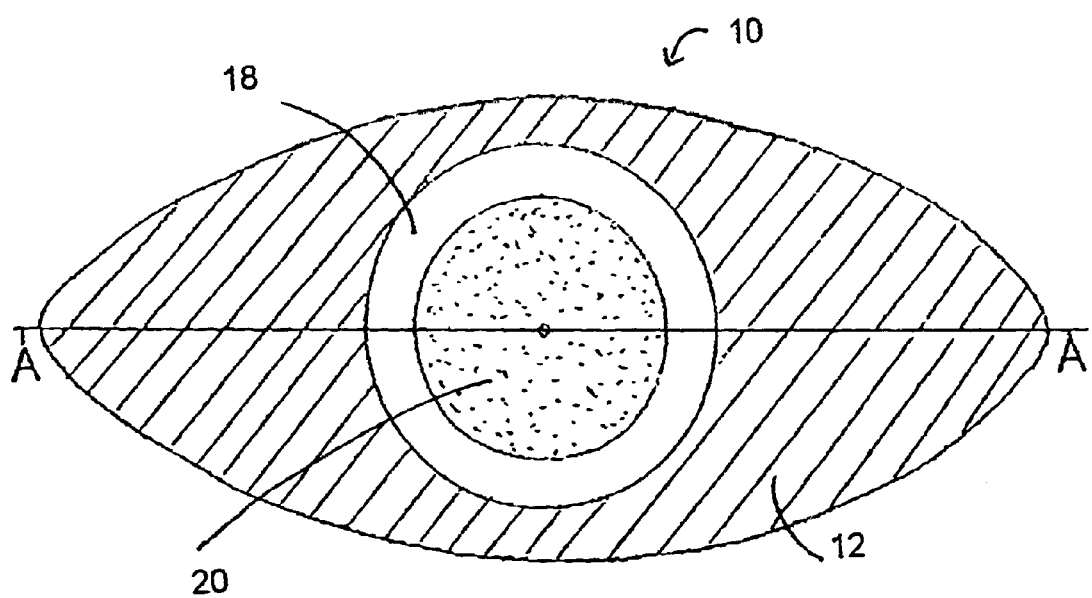
FIG. 1 is a top plan view of an everlasting candle in accordance with one embodiment of the present invention; and, FIG. 2 is an elevational cross-section of the everlasting candle of FIG. 1, taken along the line A—A in FIG. 1.
Figure 2:
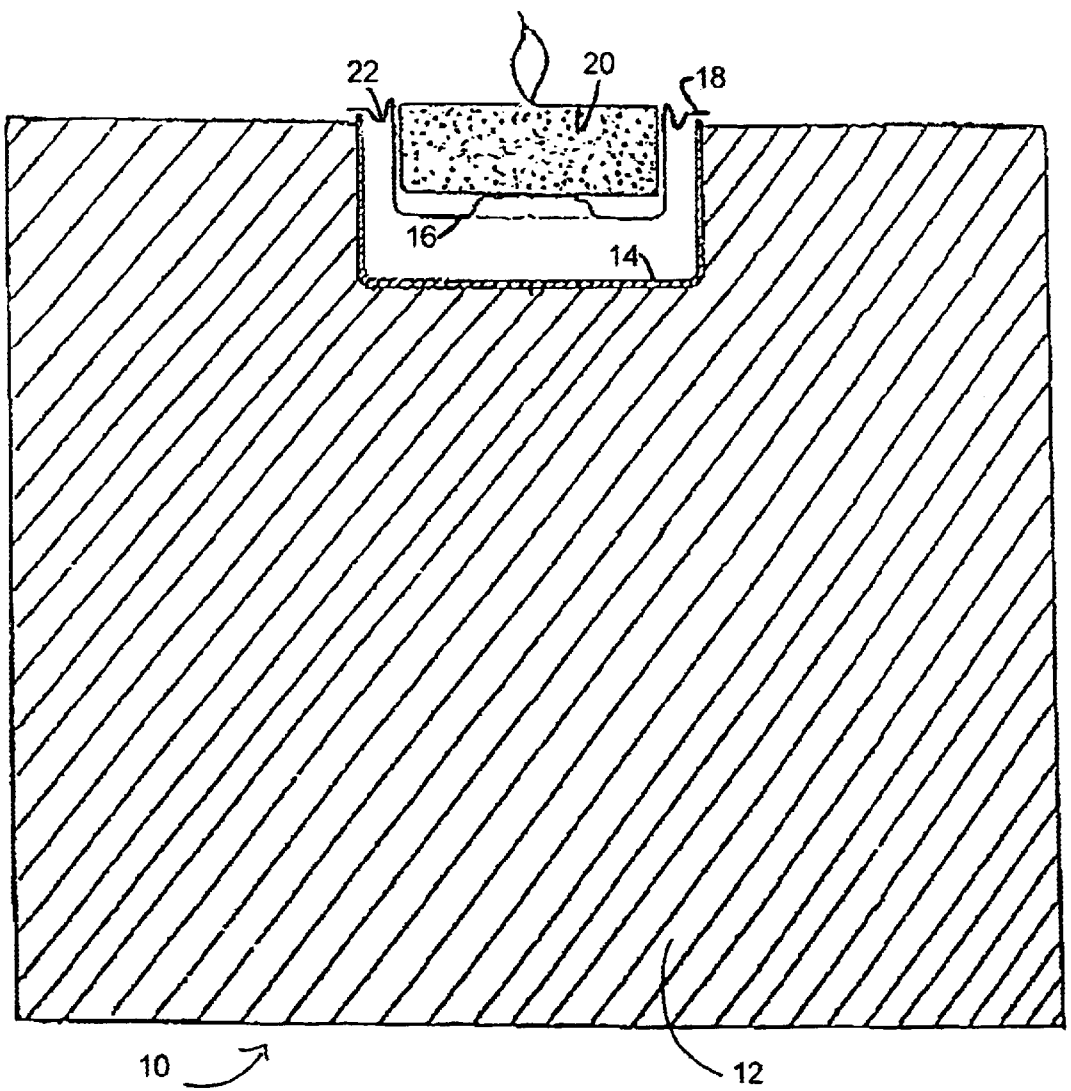

As best seen in FIG. 2, the everlasting candle 10 comprises a wax body 12 with a recessed hollow in its top, an insulating container 14 set within that hollow, a holding container 16 with an annular rim 18 set within the insulating container and communicating with the insulating container only by the rim, and a tea light votive candle 20 set within the holding container. The annular rim 18 includes a groove 22 for receiving scented aromatherapy oil or the like. The tea light votive candle 20 is, of course, preferably situated such that it is relatively flush with the top of the wax body 12 of everlasting candle 10 in order to maintain the appearance of a normal candle.

An insulative airspace 24 is maintained between the insulating container and the holding container so as to minimize the transfer of heat from a burning tea light votive candle 20 to the wax body 12, and the insulating container 14 may also be constructed of plastic or some other material having a high specific heat capacity to further lessen the transfer of heat through to the wax body 12. In the preferred embodiment, the holding container 16 is constructed of metal (or some other material having a low specific heat capacity) so that the heat from a burning tea light votive candle 20 will warm the holding container 16, thereby accelerating the evaporation of scented oil from groove 22.

As will be apparent to those skilled in the art in the light of the foregoing disclosure, many alterations and modifications are possible in the practice of this invention without departing from the spirit or scope thereof. Accordingly, the scope of the invention is to be construed in accordance with the substance defined by the following claims.

The embodiments of the invention in which an exclusive property or privilege is claimed are as follows:

1. An everlasting candle comprising;

a wax body having a recessed hollow;

an insulating container set within the hollow;

a holding container with an annular rim set within the insulating container and communicating with the insulating container only by the rim, thereby to provide an insulative airspace between the two containers; and, a tea light votive candle, the holding container being suitably configured and dimensioned to replaceably receive the tea light votive candle.

2. The everlasting candle of claim 1 wherein the annular rim is made of a material having a relatively low specific heat capacity, and wherein the rim includes a groove for receiving scented oil.

* * * * *